(12) United States Patent
Keenan et al.

(10) Patent No.: US 8,956,880 B2
(45) Date of Patent: Feb. 17, 2015

(54) DETECTION OF MICRO-ORGANISMS

(75) Inventors: Elizabeth Ann Keenan, Bolton (GB); Michael S. Brennand, Lancashire (GB)

(73) Assignee: MICAP PLC, Lancashire (GB)

( * ) Notice: Subject to any disclaimer, the term of this patent is extended or adjusted under 35 U.S.C. 154(b) by 541 days.

(21) Appl. No.: 11/382,725

(22) Filed: May 11, 2006

(65) Prior Publication Data

US 2006/0188942 A1    Aug. 24, 2006

Related U.S. Application Data

(62) Division of application No. 10/467,440, filed as application No. PCT/GB02/00498 on Feb. 5, 2002, now abandoned.

(30) Foreign Application Priority Data

Feb. 5, 2001 (GB) .................................. 0102790.3
Nov. 7, 2001 (GB) .................................. 0126674.1

(51) Int. Cl.
| | |
|---|---|
| *G01N 33/544* | (2006.01) |
| *B01D 63/02* | (2006.01) |
| *B01D 67/00* | (2006.01) |
| *B01D 69/08* | (2006.01) |
| *B01D 69/10* | (2006.01) |
| *B01D 69/14* | (2006.01) |
| *B01D 71/26* | (2006.01) |
| *C12Q 1/04* | (2006.01) |
| *C12Q 1/24* | (2006.01) |

(52) U.S. Cl.
CPC ............ *B01D 63/02* (2013.01); *B01D 67/0093* (2013.01); *B01D 69/08* (2013.01); *B01D 69/105* (2013.01); *B01D 69/144* (2013.01); *B01D 71/26* (2013.01); *C12Q 1/04* (2013.01); *C12Q 1/24* (2013.01); *B01D 63/024* (2013.01); *B01D 2323/30* (2013.01)
USPC ........... 436/535; 436/501; 436/518; 436/528; 435/7.1; 435/287.2; 435/287.8; 435/287.9

(58) Field of Classification Search
USPC .......... 422/101; 435/7.1, 287.2, 287.8, 287.9, 435/308.1; 436/501, 518, 528, 535
See application file for complete search history.

(56) References Cited

U.S. PATENT DOCUMENTS

| | | | | |
|---|---|---|---|---|
| 3,706,306 A | * | 12/1972 | Berger et al. | 600/575 |
| 4,267,053 A | * | 5/1981 | Hashino et al. | 210/650 |
| 4,647,377 A | * | 3/1987 | Miura | 210/323.2 |
| 4,714,556 A | * | 12/1987 | Ambrus et al. | 210/638 |
| 4,781,768 A | * | 11/1988 | Khare | 419/28 |
| 5,008,012 A | * | 4/1991 | Hagihara et al. | 210/321.8 |
| 5,143,612 A | * | 9/1992 | Hamanaka et al. | 210/321.8 |
| 5,211,850 A | * | 5/1993 | Shettigar et al. | 210/645 |

(Continued)

FOREIGN PATENT DOCUMENTS

| | | |
|---|---|---|
| EP | 0 302 949 | 2/1989 |
| EP | 0 439 212 | 7/1991 |

(Continued)

*Primary Examiner* — Melanie Y Brown
(74) *Attorney, Agent, or Firm* — Boyle Fredrickson, S.C.

(57) ABSTRACT

The present invention concerns methods for detecting the presence of a micro-organism in a fluid, gaseous and solid samples, together with apparatus for use in same. The invention comprises the use of a plurality of hollow fibers to filter the fluid and the capture of the micro-organisms on the membrane by means of a specific binding pair.

13 Claims, 4 Drawing Sheets

(56) References Cited

U.S. PATENT DOCUMENTS

| | | | |
|---|---|---|---|
| 5,456,835 A * | 10/1995 | Castino et al. | 210/645 |
| 5,643,455 A * | 7/1997 | Kopp et al. | 210/636 |
| 5,868,936 A * | 2/1999 | Ofsthun et al. | 210/649 |
| 6,270,674 B1 * | 8/2001 | Baurmeister et al. | 210/649 |
| 6,342,157 B1 * | 1/2002 | Hood, III | 210/321.6 |
| 6,663,745 B1 * | 12/2003 | Cheng et al. | 156/293 |
| 7,378,024 B2 * | 5/2008 | Bartels et al. | 210/636 |
| 2002/0183678 A1 * | 12/2002 | Heim | 604/6.04 |

FOREIGN PATENT DOCUMENTS

| | | | |
|---|---|---|---|
| GB | 2135902 | | 9/1984 |
| GB | 2352652 | * | 2/2001 ............ B01D 67/00 |
| WO | WO 87/03690 | | 6/1987 |
| WO | WO 94/25848 | | 11/1994 |
| WO | WO 96/04067 | | 2/1996 |
| WO | WO 98/04675 | | 2/1998 |
| WO | WO 00/23792 | | 4/2000 |

* cited by examiner

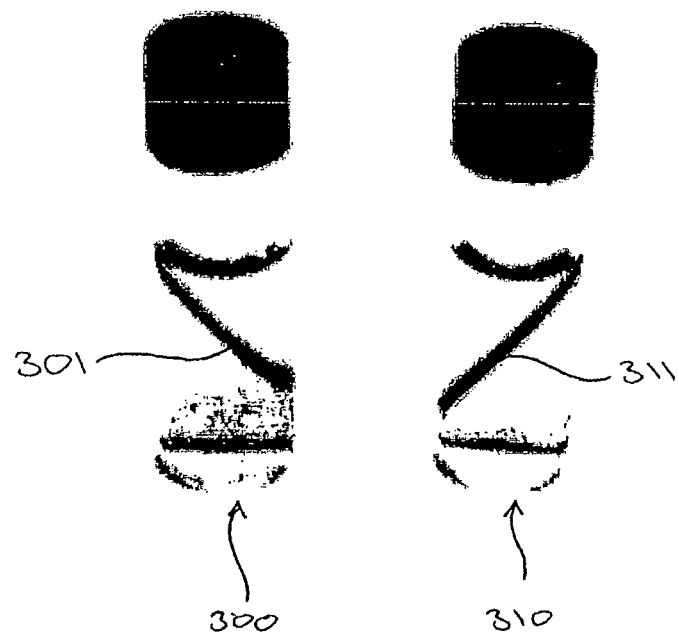

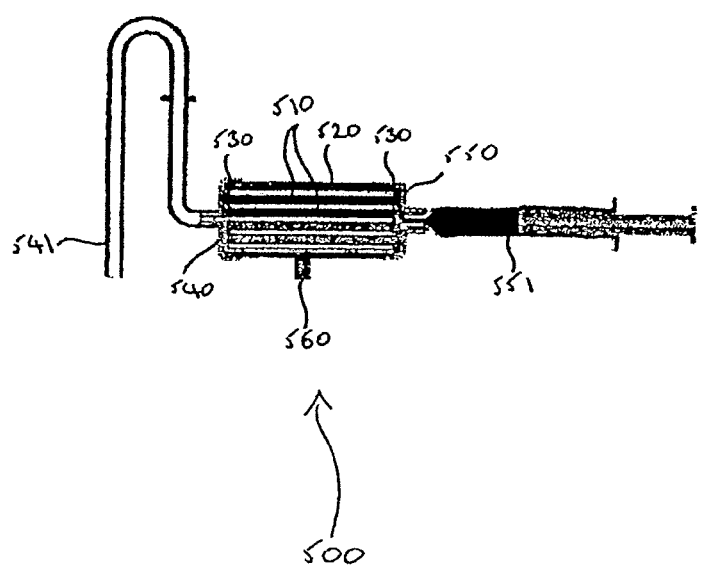

DETECTION OF MICRO-ORGANISMS

CROSS REFERENCE TO RELATED APPLICATION

This application is a divisional application of presently co-pending U.S. application Ser. No. 10/467,440, filed Aug. 5, 2003, and entitled "Detection of Micro-Organisms," the entirety of which is incorporated herein by reference.

BACKGROUND OF THE INVENTION

1. Field of the Invention

The present invention concerns improved methods for detecting micro-organisms particularly yeast and bacteria in colloidal mixtures such as beer. It is also concerned with detecting micro-organisms in air and solid samples (such as food or bacterial spores) which can be placed in a liquid phase suspension or dissolved.

The production of foodstuff and beverages such as beer is accompanied by testing for the presence of certain micro-organisms in order to ensure the quality of the end-product. The brewing process may for example require in-line testing every few hours of a sample having a volume of at least 25 ml, and preferably sample volumes of for example 250 ml. Particulate matter which may include micro-organisms, namely yeast and bacteria, must then be separated from the sample and then tested to determine the presence or absence of specific micro-organisms. Devices used to achieve this include the Bibby disposable vacuum filter unit having a flat filter with an average pore diameter of 0.45 um and the Nalgene filter holders with receivers, having a flat filter with an average pore diameter of 0.45 um or 0.2 um (see for example Merck Laboratory Supplies Catalogue 1998, p. 482). Such devices allow the filtration of maximum sample volumes of only 100 ml, have a flat surface area of 50 cm2 and can take up to 30 minutes to test a sample due to their complexity of use. Once their maximum volume has been filtered, they become blocked by particulate matter such as proteins present in the sample fluid (e.g. lager, ales and other colloidal solutions) and any subsequent filtration would require pressures so high as to cause cell lysis, preventing the detection of the micro-organisms and giving false results.

2. Description of the Related Art

Prior art devices take substantially more time to separate and detect micro-organisms from a sample than is required using the devices and methods of the present invention. WO 01/11006 discloses improvements to the prior art allowing more rapid separation and detection of micro-organisms, as well as relatively simple and easy subsequent recovery of, and thus testing for, micro-organisms. The devices and methods of the present invention are distinct from those of WO 01/11006, and in particular (as detailed below) the methods involve a washing step rather than just a resuspension step.

The devices and methods of the present invention further improve upon WO 01/11006 and the other prior art by providing a yet more rapid and simple method for the separation and detection of micro-organisms from a sample.

In particular it has been found that the devices of the present invention can rapidly detect all of the bacteria in e.g. a 100 ml volume of test solution containing as few as 1-3 bacteria. Similar results can also be achieved with larger volumes e.g. 1000 ml of lager containing 1-3 bacteria.

OBJECTS AND SUMMARY OF THE INVENTION

According to the present invention there is provided a method for detecting the presence of a micro-organism in a fluid sample, comprising the steps of:

i) passing said sample through the sample inlet of a filter device comprising a plurality of hollow fibre filter membranes which have attached to them a first member of a specific binding pair, said micro-organism displaying the second member of said specific binding pair, said membranes having first and second ends, an outer surface and an inner surface defining a lumen, said first end of each of said membranes being open and communicating with said sample inlet and flow through said second end of each of said membranes being restricted such that said flow occurs only through said first end and the pores of said membranes, the sample mixture being filtered through the pores of said membranes, leaving a filtrand in said lumen of said membranes;

ii) washing the unbound part of said filtrand from said lumen of said membranes;

iii) detecting the presence of any of said specific binding pairs attached to said membranes; and iv) correlating the results of detection step (iii) with the presence of said micro-organism in said fluid sample.

The sample may for example have a volume of at least 25, 50, 100, 200, 250, 300, 400, 500, 600, 700, 750, 800, 900 or 1000 ml.

A "member of a specific binding pair" is one of two different molecules, having an area on the surface or in a cavity which specifically binds to and is thereby defined as complementary with a particular spatial and polar organization of the other molecule. The members of the specific binding pair are commonly referred to as ligand and receptor (antiligand), sbp member and sbp partner, sbp members or the like. These are usually members of an immunological pair such as antigen-antibody, although the term does have a broader meaning encompassing other specific binding pairs.

The term "antibody" in its various grammatical forms is used herein to refer to immunoglobulin molecules and immunologically active portions of immunoglobulin molecules, i.e., molecules that contain an antibody combining site or paratope. Such molecules are also referred to as "antigen binding fragments" of immunoglobulin molecules.

By "attached" is meant that the first member of the specific binding pair is physically constrained and prevented or hindered from separating from the membrane. This may be by means of covalent binding to the membrane, for example of an antibody to the membrane, or it may be by other means, for example van der Waals' forces. Thus a first member of a specific binding pair, such as an antibody, may simply be trapped by the fibres of a membrane, and need not be covalently bound to it.

In particular antibodies and other first members of specific binding pairs may be covalently bound to polypropylene membranes by cross linking them with glutaraldehyde. Methods of cross-linking will be readily apparent to a person skilled in the art and can be achieved by e.g. oxidation or halogenation of the polypropylene groups to a reactive monomer.

In order to test samples which are not in the liquid phase, for example air samples or particulate matter or other solids such as foodstuffs, they must first be placed in a fluid suspension. There are two basic situations in which this is done: testing air or other gaseous samples for the presence of micro-organisms, and testing solids such as powders and foodstuffs for the presence of micro-organisms.

1. Testing of Gaseous Samples:

In order to test a gaseous sample such as air for the presence of a particular microorganism, an air (i.e. gas) filtration device is employed having a pore diameter sufficient to entrap the chosen micro-organism. For example, in the case of anthrax (*Bacillus anthracis*) which has a diameter of 1 urn, a pore size of e.g. 0.2 pm may be used. The air filtration device may also comprise a fan to encourage the flow of air through the filter, and a large volume of air can be passed through the filter in a relatively small period of time, all particulate matter of a greater size than the pore diameter being retained. The filter is then contacted with a sample fluid (e.g. a buffer or another solution, fluid or mixture into which the given micro-organism can be suspended or solubilised) in which the micro-organism can be suspended or solubilised, and any entrapped micro-organisms are placed into suspension or solubilised as appropriate (i.e. fluid-phase). Once this initial stage of capturing micro-organisms and placing them in suspension/solubilising them has been completed, the rest of the method of the present invention can then be worked (i.e. steps (i)-(iv) as defined above).

The exact nature of the sample fluid such as a buffer or other solution, fluid or mixture in which the given micro-organism can be solubilised or suspended is dependent upon the nature of the micro-organism itself and the first member of the specific binding pair used in step (i) above. The function of the sample fluid is to enable the given microorganism to interact with the first member of the specific binding pair such that the specific binding pair can be formed as appropriate to allow the detection of the given micro-organism. For example, the first member of the specific binding pair may form a specific binding pair with the or a given micro-organism, and thus its detection can be effected, the formation of a specific pair being correlated with the presence of the given micro-organism.

2. Testing of Solids:

In order to test a solid such as a foodstuff (e.g. cake or bread) for the presence of a given micro-organism, the solid is contacted with a sample fluid in which the micro-organism can be suspended or solubilised, and any entrapped micro-organisms are placed into suspension or solubilised as appropriate. As before, once this initial stage of capturing micro-organisms and placing them in suspension/solubilising them has been completed, the rest of the method of the present invention can then be worked (i.e. steps (i)-(iv) as defined above).

Thus according to the present invention there is also provided a method for detecting the presence of a micro-organism in a solid sample, comprising the steps of: a) contacting said solid sample with a sample fluid such that said microorganism is placed in fluid-phase, to give a fluid sample; and b) performing the method of steps (i)-(iv) upon said fluid sample.

Another example of the testing of solids is the testing of the contents of a package such as a letter. The above method is performed, namely contacting the solid with a sample fluid and then performing steps (i)-(iv) to determine the presence of the given microorganism. However, the contents of the package must first be removed. In order to achieve that, the present invention provides apparatus comprising a first chamber into which said package may be placed, a second chamber containing sample fluid, means (such as a pump or syringe) to alter the relative pressure in said first and second chambers, said second chamber communicating with said first chamber by means of a piercing implement having a lumen through which flow may occur.

The present invention also provides a method for testing the contents of a package for the presence of a given micro-organism, comprising placing said package in said first chamber, altering the relative air pressure in said first and second chambers, and contacting said package with said piercing implement such that said package is pierced and solid matter in said package, particularly particulate matter, passes from said package to said sample fluid and is suspended or solubilised in said sample fluid to give a fluid sample. The method of steps (i)-(iv) is then performed with the fluid sample and any micro-organisms therein detected.

Thus according to the present invention there is provided a method for testing the contents of a package for the presence of a given micro-organism, comprising the steps of:
a) placing said package in a first chamber which communicates by way of a piercing implement with a second chamber containing a sample fluid;
b) contacting said package with said piercing implement such that any solid material in said package is able to pass via said piercing implement to said sample fluid in said second chamber, to give a fluid sample; and
c) performing the method of steps (i)-(iv) upon said fluid sample.

The method may additionally comprise the step of effecting a relative gaseous pressure change in said first and second chambers such that the pressure in said first chamber is greater than that in said second chamber. The movement of any solid matter, such as particulate matter, from the package in the first chamber to the second chamber can thereby be encouraged or effected.

In order to allow the package to be safely removed from said apparatus, it may be provided with a self-sealing pad which is contacted with the piercing implement-upon its removal from the piercing implement the pad will self-seal, preventing any further egress of solid from the package and making it safe to remove from the apparatus.

The piercing implement may be sealed such that the seal is broken upon piercing of the package—in this way it is possible to maintain a pressure difference between the first and second chambers, the pressure being reduced in the second chamber relative to that in the first. Alternatively, the pressure in the chambers can be altered after piercing has occurred. The piercing implement may be self-sealing. Thus also provided according to the present invention is a method for testing the contents of a package for the presence of a given micro-organism, comprising placing said package in said first chamber, contacting said package with said piercing implement such that said package is pierced and solid matter in said package, particularly particulate matter, is able to pass from said sample package to said sample buffer (or said another solution, fluid or mixture into which the given micro-organism can be suspended or solubilised), and reducing the air pressure in said second chamber relative to that in said first chamber, such that said solid matter passes from said package to said sample buffer and is suspended or solubilised in said sample buffer (or said other solution, fluid or mixture into which the given microorganism can be suspended or solubilised).

Alternatively of course it is possible not to effect any pressure difference between the first and second chambers and to effect the transfer of solid matter between the two by e.g. gravity.

In all of these cases of testing gases and solids for the presence of a given microorganism the present invention provides the distinct advantage of giving rapid and accurate results. The time taken for a sample assay can be many times less than other comparable assays such as ELISA and PCR. A typical assay time using the present invention is 15 minutes.

In the case of sampling air, extremely large volumes of air may be passed through the filter (for example 10, 25, 50, 100, 250, 500, 750, 1000, 2500, 5000, 7500 or 10000 liters of air) and the retained particulate matter tested in an extremely short period of time-again an assay time of 15 minutes is typical. Thus these testing methods for micro-organisms allow for testing in previously un-suggested ways, and allow for the extremely rapid generation of results, which it has not been previously possible to achieve.

The present invention with its testing of fluid samples for the presence of microorganisms can of course also be used for the testing of fluid samples for the presence of e.g. anthrax with the use of e.g. an anti-anthrax antibody as the first member of a specific binding pair.

As well as testing for anthrax, the present invention can also be used to test for any other micro-organisms which may be used in biological warfare.

The sample is passed through the filter membranes under conditions which allow for binding of the first and second members of the specific binding pair. If it is desired or necessary to reduce the possibility of binding of moieties other than the second member of the specific binding pair to the first member of the specific binding pair, more stringent binding (also referred to as "stringent hybridisation") conditions may be used. For example, the temperature or pH may be varied to provide stringent hybridisation conditions. Appropriate hybridisation conditions will depend upon the nature of the members of the specific binding pair and will be readily apparent to one skilled in the art.

At wash step (ii), it is obviously essential that bound specific binding pairs are not washed from the lumen of the membranes, and so the washing step removes the filtrand other than any second members of the specific binding pair which have bound to the first members of the specific binding pair attached to the membranes. It is of course possible that, occasionally, a specific binding pair could become detached from the membranes and washed, together with the unbound filtrand, from the lumen of the membranes. Although this may occasionally happen, substantially all (i.e. essentially all) of the first members of the specific binding pair having bound to them second members of the specific binding pair remain attached to the membranes.

The detection step (iii) may take one of many forms. For example, the specific binding pair may be detected by the binding to the pair or to the micro-organism of a labelled probe, for example a detection antibody which incorporates an enzyme (the classical enzyme immunosorbent assay, EIA). Alternatively the probe may be a radiolabelled antibody or a fluorescently labelled antibody. Other probes will be readily apparent to a person skilled in the art.

Alternatively, the micro-organism may be eluted (i.e. separated) from the first member of the specific binding pair and a separate detection step employed. For example, eluted micro-organism can be lysed and any ATP released detected using a luciferase assay.

Alternatively, micro-organism specific antibodies may be used, or the eluate can be plated out on a general (or micro-organism specific) nutrient culture and the growth of any micro-organism colonies detected. The eluate may also be tested using oligonucleotide probes specific to the micro-organism in a conventional PCR test.

The range of detection steps available for use in the present invention also means that the membranes may have attached to them first members of a plurality of specific binding pairs. The different first members may be mixed together and attached throughout the membranes, or first members of a given specific binding pair may be attached to the membranes at a specific position. The detection step employed may allow the general detection and/or quantification of the specific binding pairs, or it may allow the detection and/or quantification of a chosen specific binding pair or pairs. For example, the presence of a first specific binding pair could be detected using a first fluorophore, and the presence of a second specific binding pair detected using a radiolabel, or by the use of a second fluorophore having an excitation and/or emission spectrum distinguishable from that of the first fluorophore.

Prior art devices typically present filtered particulate matter as a hard "biscuit" (a relatively highly compressed high density block of particulate matter) on a membrane surface, micro-organisms and other particulate matter blocking and being trapped in membrane interstices. This biscuit is difficult to remove and difficult to process to enable it to be tested for the presence of micro-organisms.

The configuration of the devices of the present invention results in the formation of a resuspendable "cake" which can be subsequently washed away, and allows the use of lower pressures during filtration, which in turn prevents the formation of a dense biscuit and the need for higher pressures. If operated at higher pressures, lysis of bacteria can occur, in turn giving incorrect results. High pressure can also cause distortion of bacteria, allowing them to pass through the membrane and giving incorrect results.

Prior art filtration device and methods include those of GB 2135902, EP 302949, WO 94/00222, WO 84/00015, U.S. Pat. No. 5,863,501, U.S. Pat. No. 5,814,179, U.S. Pat. No. 4,501, 793, JP 4-135478 (WPI Abstract 1992-205001), JP 63-104615 (WPI Abstract 1988-165566), JP 63-088007 (WPI Abstract 1988-145060) and JP 61-133105 (WPI Abstract 1986-200908). However, none of them disclose or suggest the methods of the present invention including each of the steps necessary to obtain the results which they are capable of providing. In particular, the prior art does not suggest producing a filtrand in the form of a re-suspendable "cake" rather than a more solid "biscuit", nor does the prior art suggest washing the filtrand from the membranes as part of a subsequent processing step.

For example, JP 63-104615 discloses a device for separating e.g. viruses from fluids, comprising a plurality of porous hollow cellulose fibres, one end of them being embedded in a filler material and open to the atmosphere, and the other end being sealed. However, it does not suggest the specific methods of the present invention, nor their advantages. Other filtration devices are also known from e.g. the "CultureGard Hollow Fiber Filter" from Cole Parmer (www.coleparmer.com), product code EW-29510-50.

Advantageously, it has been found that polypropylene fibre membranes may be used (the Cole Parmer product above uses cellulose hollow fibre membranes).

In particular, membranes can be treated with a wetting agent such as iso-propanol and/or a detergent such as Tween-20 to make them more hydrophilic and susceptible to the attachment of the first member of the specific binding pair. The surprisingly good results achieved by treating membranes with iso-propanol prior to attaching antibodies to them are shown below. For example, a membrane can be soaked in iso-propanol and then allowed to dry, prior to treatment with Tween 20 (typically, 0.1%) and antibody.

By pre-treating the membranes with a wetting agent such as an alcohol it has been found that the rate of flow of the sample mixture through the membranes is increased massively. This is particularly true when comparing dried treated membranes with dry untreated membranes. This increased flow rate ensures that micro-organisms are collected without causing their lysis or forcing them through the membranes.

Useful detergents include non-ionic detergents, particularly Tween 20, more particularly a solution of 5% Tween 20.

The use of a plurality of hollow fibre filter membranes also provides a relatively large surface area (typically at least three times as much) across which filtration may take place, when compared to the surface area provided by a single device of similar overall dimensions (i.e. size) having a single flat membrane. This also allows for the filtering of a relatively large volume of sample prior to any blockage of pores occurring. This is particularly useful with turbid samples (e.g. stout) which contain large amounts of particulate matter which can rapidly block flat filter membranes.

The exact nature of the filter membrane material has also been found to be important—commercially available polypropylene hollow fibre membranes having an average pore diameter of 0.2 um pre-treated with iso-propanol have been found to allow much greater flow rates than e.g. polysulfone membranes having an average pore diameter of 0.2 m, even when identically pre-treated. Thus in a preferred embodiment of the present invention, the hollow fibre membrane is a polypropylene membrane. Naturally, other membranes may also be used, particularly those having similar physical characteristics e.g. a similar average pore diameter and area of pores per unit area of membrane surface, and these include the likes of polysulfone, cellulose acetate and nylon membranes.

Hollow fibre membranes used in the present invention may have an average pore diameter of 0.2 urn.

Also provided according to the present invention is a device having a sample inlet and a plurality of hollow fibre filter membranes which have attached to them a first member of a specific binding pair, the second member of said specific binding pair being displayed by a given micro-organism, said membranes having first and second ends, an outer surface and an inner surface defining a lumen, said first end of each of said membranes being open and communicating with said sample inlet and flow through said second end of each of said membranes being restricted such that said flow occurs only through said first end and the pores of said membranes, such that a sample mixture passed into said device through said sample inlet is filtered through the pores of said membranes, leaving a filtrand in said lumen of said membranes.

The ease of testing for micro-organisms using the methods and devices is supplemented by the speed of filtration—as is seen from experimental results, the present invention allows for the detection of specific micro-organisms in a given volume of sample fluid in a fraction of the time required by other devices, and is frequently at least ten times as fast.

The present invention also provides the important advantage of providing consistent results for a given sample, even when a highly turbid mixture is being filtered at least 99% consistency between different sets of results is readily achievable. This compares favourably to results obtained using flat membranes, which can be relatively inconsistent.

In various embodiments of the present invention, the hollow fibre membranes consist of polypropylene, which is used in many biomedical applications due to its low capacity for absorbing proteins. It has not been previously suggested that polypropylene membranes should have antibody or other members of specific binding pairs attached to them. In particular, the present invention shows that by treating the polypropylene membranes with iso-propanol as described herein, the specific binding pair members remain attached to the membranes even when washed with detergents such as SDS and Tween-20. This has not previously been suggested.

The invention will be further apparent from the following description, with reference to the several figures of the accompanying drawings, which show, by way of example only, one form of filter device.

BRIEF DESCRIPTION OF THE DRAWINGS

Of the Figures:
FIG. 3 shows a photograph of polypropylene membranes having attached to them antibodies, one membrane (Tube A, left) having been pre-treated by soaking overnight in carbonate/bicarbonate buffer, and the other (Tube B, right) having been pre-treated by soaking overnight in iso-propanol;
and
FIG. 4 shows an alternate filter device used in the present invention.

DETAILED DESCRIPTION OF THE PREFERRED EMBODIMENTS

Figure 1:
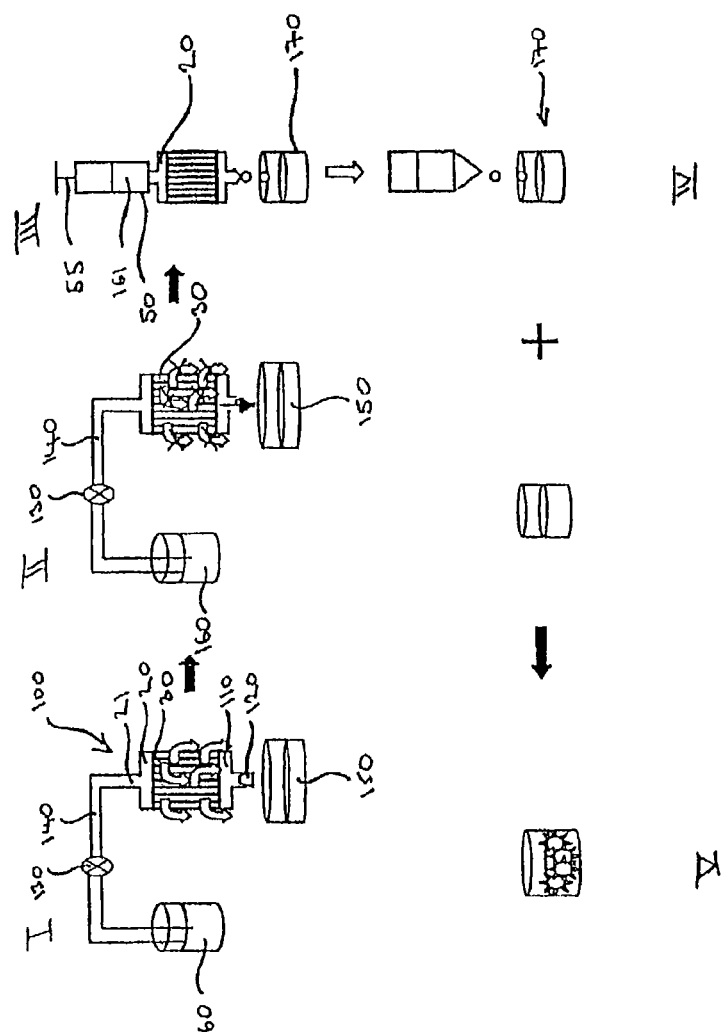
FIG. 1 shows first device according to the present invention and its use in a method of detection of micro-organisms.

Unless stated otherwise, all procedures were performed using standard protocols and following manufacturer's instructions where applicable. Standard protocols for various techniques including PCR, molecular cloning, manipulation and sequencing, the manufacture of antibodies, epitope mapping and mimotope design, cell culturing and phage display, are described in texts such as McPherson, M. J. et al. (1991, PCR: A practical approach, Oxford University Press, Oxford), Sambrook, J. et al. (1989, Molecular cloning: a laboratory manual, Cold Spring Harbour Laboratory, New York), Huynh and Davies (1985, "DNA Cloning Vol I-A Practical Approach", IRL Press, Oxford, Ed. D. M. Glover), Sanger, F. et al. (1977, PNAS USA 74 (12): 5463-5467), Harlow, E. and Lane, D. ("Using Antibodies: A Laboratory Manual", Cold Spring Harbor Laboratory Press, New York, 1998), Jung, G. and Beck-Sickinger, A. G. (1992, Angew. Chem. Int. Ed. Eng., 31: 367-486), Harris, M. A. and Rae, I. F. ("General Techniques of Cell Culture", 1997, Cambridge University Press, ISBN 0521 573645), "Phage Display of Peptides and Proteins: A Laboratory Manual" (Eds. Kay, B. K., Winter, J., and McCafferty, J., Academic Press Inc., 1996, ISBN 0-12-402380-0).

Reagents and equipment useful in, amongst others, the methods detailed herein are available from the likes of Amersham (www.amersham.co.uk), Boehringer Mannheim (www.boehringer-ingeltheim.com), Clontech (www.clontech.com), Genosys (www genosys.com), Millipore (www.millipore.com), Novagen (www.novagen.com), Perkin Elmer (www.perkinelmer.com), Pharmacia (www.pharmacia.com), Promega (www.promega.com), Qiagen (www.qiagen.com), Sigma (www.sigma-aldrich.com) and Stratagene (www.stratagene.com).

Where "PMID:" reference numbers are given for publications, these are the PubMed identification numbers allocated to them by the US National Library of Medicine, from which full bibliographic information and abstract for each publication is available at www.ncbi.nlm.nih.gov. This can also provide direct access to electronic copies of the complete publications, particularly in the case of e.g. PNAS, JBC and MBC publications.

Antigens specific to *Lactobacillus brevis* are well known in the art, for example from Yasui T, and Yoda K. (Appl Environ Microbiol. 1997 November; 63 (11):4528-33; PMID: 9361439), Yasui T, Yoda K. (FEMS Microbiol Lett. 1997 Jun. 15; 151(2):169-76; PMID: 9228750), and Shimohashi H, Kodaira S, and Suegara N. (Jpn J Microbiol. 1976 October; 20(5):405-13; PMID: 62862), as are anti-*Lactobacillus brevis* antibodies (see for example Youichi Tsuchiya, Yasukazu Nakakita, Junji Watari, and Ken Shinotsuka, 1999

American Society of Brewing Chemists (ASBC) Annual Meeting in Phoenix, Ariz., June 19-23, Abstract 0-17).

Antibody Preparation

A highly concentrated solution of *L. brevis* micro-organisms was killed by addition of an 8% formaldehyde solution at room temperature for 2-3 hours. The cell pellet was obtained by centrifugation at 12000 rpm for 10 minutes. The liquid was removed and the cell pellet washed and resuspended in sterile deionised water. The centrifugation and washing procedure was repeated until all formaldehyde traces had been removed. Resuspension of the final cell pellet (immunogen) in 0.5 ml PBS and stored frozen until required. Prior to injection of the immunogen 0.125 ml of immunogen was diluted with equal parts Freunds complete adjuvant (Sigma-Aldrich Inc, catalogue number F5881).

This provides the primary injection with three subsequent booster injections that have the immunogen diluted in equal parts of Freunds Incomplete Adjuvant (Sigma-Aldrich Inc, catalogue number F5506). A sample of the resuspended antigen preparation was also tested by plating out and enumeration to ensure that no viable cells remained. Immunoglobulins are purified from serum by protein A affinity chromatography supplied by Sigma-Aldrich Inc, catalogue number PURE-1A.

Hollow Fibre Membrane Pre-Treatment

Hollow fibre polypropylene membranes (Membrana, Wuppertal, Germany; catalogue number PP Q3/2) having a nominal pore size of 0.2 micron and length of 55 cm, were immersed overnight in iso-propanol. The membranes were then dried followed by immersion in Tween-20 (5%) for 20 minutes and then dried.

Hollow Fibre Membrane Preparation

Thirty-five lengths of the pre-treated hollow fibre membranes (above) were bundled together at one end. UV cure adhesive was applied to a small section of the membranes, and after application a 5 mm collar was then slipped over the adhesive area. UV light was then applied until the adhesive was cured (45 seconds). All membranes were examined to ensure that the lumen of the membrane was fully open. A cap with a syringe fitting was then fitted to the collar and secured using UW cure adhesive. 5 ml of a 1:10,000 dilution of anti-*L. brevis* antibody (dilution carried out in 0.1 M carbonate/bicarbonate buffer (Sigma, catalogue number C3041)) was placed into a syringe and attached to the cap of the membranes. The other end of the membranes was closed using forceps and the solution applied such that the lumen of the membrane was wetted with solution. Application was stopped when the solution could be seen on the outer surface of the membrane indicating that all of the surfaces of the membrane had been coated with the solution. The membranes were then sealed into hybridisation tubing and incubated at room temperature for 15 minutes.

Unbound antibody was then removed by passing air through the lumen of the membrane followed by washing the lumen with several applications of phosphate buffered saline (PBS) containing 0.1% Tween 20 (~50 ml per application). The coated membranes were then allowed to dry completely.

Hollow Fibre Membrane Testing

To demonstrate the effect of pre-treatment with iso-propanol upon the attachment of antibody to polypropylene hollow fibre membranes, two tubes were prepared (see FIG. 3), one (Tube A, 300) containing polypropylene hollow fibre membrane 301 which had been soaked overnight in carbonate/bicarbonate buffer prior to being immersed in swine antibody linked to HRP (horse radish peroxidase, Dako) for 60 minutes. The other tube (Tube B, 310) contained polypropylene hollow fibre membrane 311 which had been soaked overnight in iso-propanol prior to being immersed in swine antibody linked to HRP (horse radish peroxidase, Dako) for 60 minutes. Both of membranes 301,311 were then kept in buffer containing 0.1% Tween 20, and extensively washed.

To determine the extent of antibody attachment, two drops of TMB (tetra methyl benzadine) chromogenic reagent are dispensed into each of two glass vials (not shown) containing 1.5 ml HRP substrate, and each of membranes 301, 311 dipped into one of the vials, and colour change indicative of the presence of antibody allowed to develop.

Results are shown in FIG. 3. Darker patches of the membranes 310,311 indicate colour change caused by HRP, i.e. the attachment of antibodies to the membrane. Membrane 311 is substantially darker than membrane 310, indicating that substantially more antibody is attached to it.

Quantification of Binding

To quantify binding of micro-organisms to antibody attached to hollow fibre membranes, a 100 ml sample containing a known concentration of *L. brevis* is passed through the filter device, washed using PBS in 0.1% Tween-20 (as above) to remove unbound micro-organisms and the bound micro-organisms eluted using buffer (typically 0.1 M citric acid pH 3.0). The eluted micro-organisms are then plated onto microbiological plates to determine the level of capture.

Specificity of Binding

To show specificity of the membrane a 100 ml solution containing known concentrations of mixed micro-organisms is applied to the filter and the above procedure followed. Only the target micro-organisms, i.e. *L. brevis*, is detectable on microbiological plating, all other micro-organisms having been washed from the membrane prior to elution.

Filter Devices

Filter device 100 comprises a sample inlet 20 having Luer lock fitting 21 communicating with 35 hollow polypropylene fibre membranes 30 having an average pore diameter of 0.2 pm. At sample inlet 20, the first ends of membranes 30 are embedded in UV-curable adhesive which holds them in place and allows then to communicate with sample inlet 20. At outlet 110, the second ends of membranes 30 are embedded in UV-curable adhesive which holds them in place and allows then to communicate with outlet 110, which is closed by plug 120, thereby restricting flow through the second ends of membranes 30. Membranes 30 have been prepared as described in the "Hollow Fibre Membrane Preparation" section above.

In use, at Stage I a 100 ml volume of lager 60 is pumped by peri pump 130 at a rate of 100 ml/minute through tubing 140 into device 100 (the volume of sample such as lager filtered through the device 100 can be increased to e.g. 1000 ml or greater by simply adjusting the surface area of membrane). As device 100 fills with lager 60, plug 120 blocking exit 110 causes the only exit from device 100 to be the pores in membranes 30, and lager 60 is therefore filtered through membranes 30 and the filtrate collected in waste collection vessel 150 and discarded.

At Stage II, plug 120 is removed and 50 ml of wash buffer 160 consisting phosphate buffered saline containing 0.01% Tween 20 is pumped through tubing 140, passing along the lumen of membranes 30 (i.e. not through the pores of the membranes 30) and collected in waste vessel 150 and discarded. When wash buffer 160 has completed passing through device 100, pump 130 is left running for an additional 10 seconds in order to pump air though tubing 140 and membranes 30 to remove excess fluid from membranes 30. Pump 130 is then turned off and device 100 separated from tubing 140 and pump 130.

At Stage III, a 1 ml sterile syringe containing 0.5 ml of elution buffer 161 (lysis buffer consisting 0.2 M NaOH) is then attached to sample inlet 20 and plunger 55 of syringe 50 fully depressed to flush elution buffer 161 through membranes 30. Plunger 55 is then drawn back and elution buffer 161 drawn back through the lumen of membranes 30. This is repeated a further two times to ensure that all bound micro-organisms have been lysed. Plunger 55 is then fully depressed to expel elution buffer 161 into sterile 1.5 ml tube 170.

At step IV, an equal volume of neutralising buffer (0.2 M Tris phosphate) is added to tube 170, a lid placed on tube 170 and its contents mixed by inverting tube 170 2-3 times.

Finally, at Stage V, an ATP assay is performed on the sample using a Biotrace Unilite luminometer and Sigma Bioluminescence reagents.

Obviously, a wide range of micro-organism detection methods may be employed, such as PCR and plating out (as described above) and so steps III-V may be modified as appropriate. For example, elution step III could be performed using 0.1 M citric acid pH 3.0 to elute whole micro-organisms into tube 170 without lysis.

ATP Assays

The most common and rapid method to determine microbial contamination is the measurement of cellular ATP. This requires the breakdown of the cell membrane/wall (cell lysis) in order to release the ATP present in the cell. The released ATP can then be determined using an enzymatic reaction that converts a substrate (luciferin) and ATP into a number of products including light. The amount of light can then be measured using a standard luminometer. A number of ATP assays are commercially available. However, the ability to lyse to completion and therefore release all cellular ATP is micro-organism strain-dependent.

Figure 2:
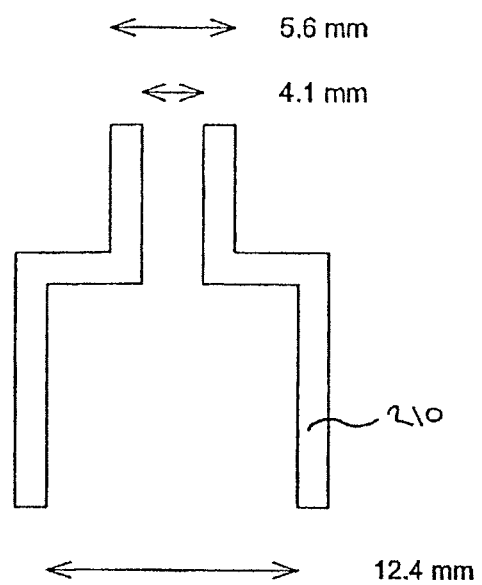
FIG. 2 shows a section through an end cap and a top view of a collar of the device of FIG. 1.
Figure 2:
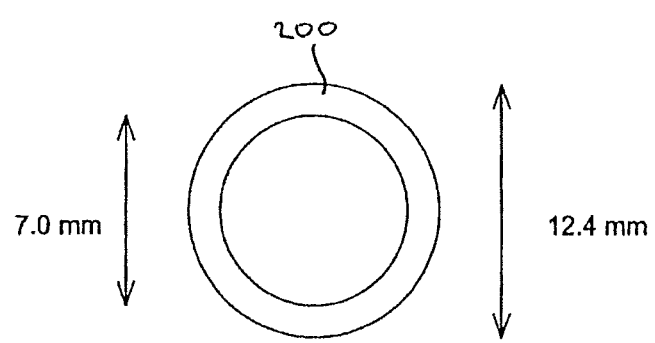

Construction of filtration devices as illustrated by the second filtration device (FIG. 2):

Apparatus:

1. Polypropylene hollow fibre membranes having an average pore diameter of 0.2 um (pre-treated with 5% Tween 20)
2. Loctite® 21 semi-automatic controller incorporating hand-held applicator and foot switch, with pressure set to 0.2 bars and digital output to 35.0.
3. Bondmatic 850 UV light source, with timer set to 40 seconds.
4. Collars (FIG. 2,200) (polycarbonate rod) having internat diameter of 7.0 mm and outer diameter of 12.4 mm.
5. Y-shaped end caps (FIG. 2,210) made from 2 mm polymer polypropylene, having a wide end (internal diameter 12.4 mm) for receiving collars and a narrow end (internal diameter 4.1 mm) for connection with Luer syringe nozzle.

Filtration devices were prepared as follows:

1. Clean all work surfaces with IPA (isopropyl alcohol).
2. Taking a bundle consisting of an appropriate number of lengths of the polypropylene hollow fibre membranes, place a plurality of collars around the bundle.
3. At a position approximately 30 mm from the end of the bundle of hollow fibre membranes, the nozzle of the adhesive applicator is placed in the centre of the membrane bundle and adhesive applied such that it penetrates through the membrane bundle and the nozzle manipulated such that adhesive is applied to all of the of membranes in the area. Adhesive is additionally applied to the outside of the bundle at the position. A collar is then slid and rotated over the membranes at the position such that it contacts the adhesive.
4. Place the adhesive-covered section of the bundle under the UV light source to cure the adhesive.
5. Apply adhesive as detailed in Step 3 (above) at a position approximately 30 mm along the bundle from the previous collar. Slide and rotate over the adhesive first and then second collars such that they contact one another, and then separate them by 1-2 mm, and repeat step 4.
6. Repeat step 5 until the whole of the membrane length has collars in place.
7. Cut the fibres in the 1-2 mm gap between the pairs of collars to give a plurality of hollow fibre devices, the fibres having open lumens at either end, and being sealed on their outside at either end with a collar.
8. Taking one of the devices and a pair of end-caps, apply loctite primer 770 to the inside rim of the end caps and around the outside of the device collars. Leave for approximately 1 minute, then apply Loctite fast set adhesive 403 around the outside of each collar and press end caps firmly over collars until bonded.

As mentioned above, results obtained using the devices and methods of the present invention show that it is possible to achieve the simple, rapid, and accurate detection of a small number of micro-organisms from a large volume of sample liquid.

As shown in FIG. 4, filter device 500 comprises 20 hollow fibre polypropylene membranes 510 of 40 mm length contained in filter body 520, each of membranes 510 being isolated in a groove in body 520 and held in place at either end by adhesive 530 which is placed on the outside of membranes 510 and which does not enter into the lumen or ends of membranes 510. Snap-fit end-cap 540 has a connector for tubing 541 so that samples can be fed directly from sample tanks into device 500. Snap-fit end-cap 550 comprises a foil-sealed cap having a connector for tubing (not shown) which, when the foil seal is intact, means the only route for fluid flow out of device 500 is by filtration through membranes 510. Upon piercing of the foil seal by e.g. syringe 551, flow is able to occur other than by filtration meaning that micro-organisms not bound to antibodies attached to membranes 510 can be washed off.

Outer body 520 of device 500 also comprises a port 560 to which can be attached a vacuum device to further encourage filtration through membranes 510.

In order to simplify the above steps of applying adhesive to the hollow fibre membranes, instead of using a UV curable adhesive and applicator (e.g. syringe) which requires contact to be made with the membranes and which might result in contamination, an alternative is to use a combination of a glue (such as an epoxy resin) and a centrifuge. Briefly, a bundle of hollow fibre membranes can be placed in a pot together with an epoxy resin and centrifuged (e.g. at 750 rpm) so as to cause the epoxy resin to form a seal around one end only of the hollow fibre membrane bundle, centrifugation continuing until the resin has set.

The membrane bundle can then be inverted and the process repeated so as to seal the other end of the membranes. Additional curing of the adhesive can be achieved by e.g. baking. In order to stop adhesives and membranes becoming stuck in e.g. the centrifuge, parts can be pre-treated by wiping them with a release agent such as Promol K502.

The sealed membrane ends can then be cut through the epoxy resin plugs so as to provide a bundle of un-blocked hollow fibre membranes terminating at either end in an epoxy resin plug. This can then be employed in the same way as the bundles made using UV curable adhesive.

Examples of useful epoxy resins are the Pur System Adhesive 725A and Pur System Adhesive 725BF.

We claim:

1. A device comprising:
   a sample inlet, an outlet tube, and a plurality of hollow fiber filter membranes each having in inlet in fluid communication with the sample inlet and an outlet in fluid communication with the outlet tube, and a removable plug that is selectively insertable into an opening of the outlet tube, wherein the fiber filter membranes have attached to them a first member of a specific binding pair, a second member of said specific binding pair being displayed by a given micro-organism, said membranes having first and second ends, an outer surface and an inner surface defining a lumen, said first end of each of said membranes being open and communicating with said sample inlet, and flow through said second end of each of said membranes being selectively restricted by selective insertion of the removable plug into the opening of the outlet tube such that, 1) when the plug is inserted into the opening of the outlet tube, said flow occurs only through said first end and the pores of said membranes, such that a sample mixture passed into said device through said sample inlet is filtered through the pores of said membranes, leaving a filtrand in said lumen of said membranes, and 2) fluid flows out of the second end—only when the plug is not inserted into the opening of the outlet tube.

2. The device according to claim 1, wherein said first member of a specific binding pair is an antibody or an antigen binding fragment thereof.

3. The device according to claim 1, wherein said membranes are selected from the group consisting of: polypropylene, polysulfone, cellulose acetate and nylon membranes.

4. The device according to claim 1, wherein said first member is covalently bound to said membranes.

5. The device according to claim 4, wherein said first member is covalently bound to said membranes by cross linking said first member with glutaraldehyde.

6. The device according to claim 1, wherein said first member is trapped by said fibers of said membrane.

7. The device of claim 1, wherein the membranes are constructed of polypropylene.

8. The device of claim 1, wherein the membranes have an average pore diameter of 0.2 pm.

9. The device of claim 1, wherein said first and second ends of the membranes are embedded in a UV-curable adhesive to hold the membranes in place.

10. The device of claim 1, further comprising an end cap disposed at the first end of the membranes.

11. The device of claim 10, wherein the end cap comprises a foil-sealed cap configured to be pierced by a syringe.

12. The device of claim 1, further comprising a port configured to be attached to a vacuum device and configured to encourage filtration through the membranes.

13. A micro-organism filtration device, comprising:
a sample inlet tube;
an outlet tube;
a removable plug that is selectively insertable into an opening of the outlet tube; and
a plurality of hollow fiber filter membranes each having an inlet in fluid communication with the sample inlet and an outlet in fluid communication with the outlet tube, wherein the filter membranes have an average pore diameter of 0.2 pm and have attached to them a first member of a specific binding pair, a second member of said specific binding pair being displayed by a given micro-organism, said membranes having first and second ends, an outer surface and an inner surface defining a lumen, said first end of each of said membranes being open and communicating with said sample inlet, and wherein flow through said second end of each of said membranes is selectively restricted by insertion of the removable plug into the opening of the sample outlet such that said flow occurs only through said first end and the pores of said membranes when the plug is inserted into the opening of the outlet tube, such that a sample mixture passed into said device through said sample inlet is filtered through the pores of said membranes, leaving a filtrand in said lumen of said membranes, and wherein fluid flows out of the second end only when the plug is not inserted into the opening of the outlet tube.

* * * * *